United States Patent [19]

Kono

[11] Patent Number: 4,457,896
[45] Date of Patent: Jul. 3, 1984

[54] APPARATUS AND PROCESS FOR FLUIDIZED SOLIDS SYSTEMS

[75] Inventor: Hisashi O. Kono, Evanston, Ill.

[73] Assignee: Institute of Gas Technology, Chicago, Ill.

[21] Appl. No.: 404,284

[22] Filed: Aug. 2, 1982

[51] Int. Cl.³ .................. F27B 15/08; C10G 35/00
[52] U.S. Cl. .................. 423/659; 208/164; 422/142; 422/145
[58] Field of Search .................. 423/659, DIG. 16; 422/142, 145; 208/10, 164

[56] References Cited

U.S. PATENT DOCUMENTS

| | | | |
|---|---|---|---|
| 2,367,694 | 1/1945 | Snuggs | 208/164 |
| 2,378,607 | 6/1945 | Watts | 422/145 |
| 2,399,050 | 4/1946 | Martin | 422/145 |
| 2,433,726 | 12/1947 | Angell | 422/145 |
| 2,579,678 | 12/1951 | Kuhn | 208/164 |
| 2,962,362 | 11/1960 | Moorman | 422/142 |
| 3,011,969 | 12/1961 | Mader | 422/145 |
| 3,079,222 | 2/1963 | Reeve | 422/142 |
| 3,661,799 | 5/1972 | Cartmell | 208/164 |
| 3,702,819 | 11/1972 | Metrailer | 423/DIG. 16 |
| 3,754,051 | 8/1973 | Suzukawa et al. | 208/164 |
| 4,013,543 | 3/1977 | Greene | 208/8 R |
| 4,026,674 | 5/1977 | McDonald | 423/659 |
| 4,398,594 | 8/1983 | Klaren | 422/145 |
| 4,402,822 | 9/1983 | Hildebrant et al. | 208/10 |
| 4,404,084 | 9/1983 | Huibers et al. | 208/10 |

FOREIGN PATENT DOCUMENTS

| | | | |
|---|---|---|---|
| 509666 | 2/1955 | Canada | 423/659 F |
| 1019646 | 11/1957 | Fed. Rep. of Germany | 423/659 F |

*Primary Examiner*—Gary P. Straub
*Attorney, Agent, or Firm*—Thomas W. Speckman

[57] ABSTRACT

An apparatus and process for fluidized solids systems used in chemical and thermal processes wherein homogeneous, dense, fluidized bed conditions are attained at high superficial gas velocities with reduced back mixing of gases by use of multiple vertically arranged fluidized bed zones interconnected by downcomer conduits extending from the lower portion of an upper bed to the lower portion of a lower bed to provide high solids circulation.

28 Claims, 3 Drawing Figures

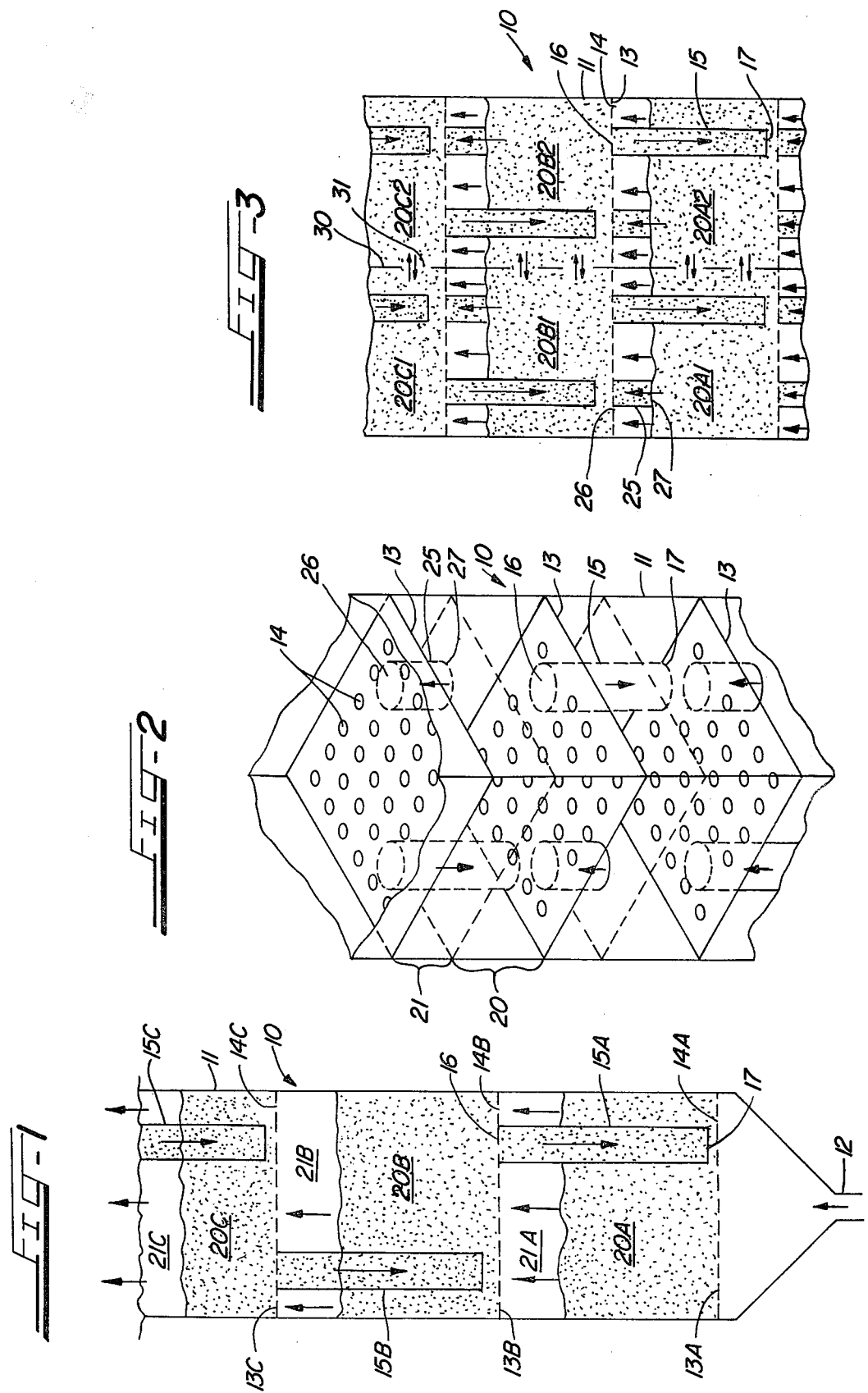

APPARATUS AND PROCESS FOR FLUIDIZED SOLIDS SYSTEMS

BACKGROUND OF THE INVENTION

1. Field of the Invention

This invention relates to apparatus and process for fluidized solids systems for use in chemical and thermal processes. More particularly, this invention relates to attaining homogeneous, dense fluidized bed conditions at high superficial gas velocities with controllable back mixing of gases and solids by use of multiple vertically arranged fluidized beds interconnected by downcomer pipes extending from the lower portion of an upper bed to the lower portion of a lower bed. High amounts of solids circulation between vertically disposed fluidized beds aid in homogeneous fluidization at higher superficial gas velocities.

2. Description of the Prior Art

Fluidized beds of solids are used in a wide variety of processes for improved fluid-solid contacting to enhance physical reactions, such as heat transfer, and chemical reactions between gases and solids and to provide a media for conduct of chemical reactions utilizing solid catalysts.

A major difficulty with prior fluidized bed reactors has been scaling them up from laboratory units to industrial plants. The most important requirement for successful scale-up is to retain a homogeneous fluidized bed since in a non-homogeneous fluidized bed the size of the bed affects the behavior of the solids as more fully described in Van Heerden, J. J., "Mixing Patterns in Large-Scale Fluidized Bed", in Grace, J. R. and Matsen, J. F., Eds., *Fluidization*, 69. New York: Plenum Press (1980). A homogeneous fluidized bed has been defined as one in which the bubbles are relatively small and both the circulation flow of solids and the gas-solid contact are intense and in which the minimum bubble formation velocity is higher than the minimum fluidization velocity. For further explanation of the types of gas fluidization see Geldart, D., "Type of Gas Fluidization", *Powder Technology* 1, 285 (1972). Solid particles having a mean diameter of less than about 100 micrometers must be employed to obtain a homogeneous fluidization state as pointed out more fully in Van Swaaij, W. P. M., "Gas-Solids Fluid Bed Reactors", *A.C.S. Symp. Ser.* 72, 1973 (1978). However, it has been found that even with utilization of such fine particles the undesired formation of large bubbles cannot be avoided in the fluidized bed as more fully pointed out in Yerushalmi, J. and Squires, A. M., "The Phenomenon of Fast Fluidization", *A.I.Ch.E. Symp. Ser.* 73, 44 (1977). In an attempt to solve this problem, Yerushalmi and Squires proposed a very fast fluidized bed which, however, has the disadvantages that there is no dense phase and that a large amount of the solid particles are carried from the fluidized bed and must be recycled through a separator, such as a cyclone. Use of internal baffles for controlling gas flow pattern in fluid bed reactors has been summarized by Harrison, D. and Grace; J. R., "Fluidized Bed with Internal Baffles", in Davidson, J. F. and Harrison D. *Fluidization*. 559, New York: Academic Press, (1971). A disadvantage of using conventional internal baffles is the inherent sacrifice of a homogeneous fluidization state. On the other hand, it has been proposed to use baffled multi-stage fluidized beds using coarse solid particles to attain a countercurrent contact of gas and solids in the two stages as described in Guigon, P., et al, "Particle Interchange Between Stages in a Baffled Fluidized Bed", *A.I.Ch.E. Symp. Ser.* 70, 63 (1974). The high solids interchange rate between two stages of a baffle fluidized bed is not conducive to homogeneous fluidization but is an attempt to achieve countercurrent flow of solids and gas.

Multiple fluidized beds arranged vertically have been utilized with solids transfer between beds. The prior art has also taught various systems of baffles for the mechanical distribution of fluids to obtain better fluid-solids contact. It is known to the art to have multiple vertically arranged fluidized beds with overflow downcomers with solids from an upper bed overflowing into the downcomer for transport to a lower fluidized bed. U.S. Pat. No. 2,639,973 teaches overflow downcomers providing solids to the upper portion of a lower bed; U.S. Pat. Nos. 2,684,840; 2,698,321; 2,891,846; 2,890,106; 3,910,769 and French Patent No. 1,058,923 teach overflow downcomers for transfer of solids from the upper surface of an upper fluidized bed to the central or lower portion of a lower fluidized bed. U.S. Pat. No. 4,017,585 teaches transfer of solids from the lower portion of an upper fluidized bed to above the top surface of a lower fluidized bed. The cited patents recognize the desirability for improving the gas-solids contacting characteristics of fluidized beds and desirability of control of the fluidized bed reaction conditions.

Solids transfer for heat supply between two vertically arranged fluidized beds utilizing riser pipes from the upper portion of a lower fluidized bed to the lower portion of an adjacent upper fluidized bed and downcomers from the lower portion of an upper fluidized bed to the lower portion of an adjacent lower fluidized bed have been suggested in the publication Kono, H. and Ninomiya, K., "Heat Supply System for a Fluidized Bed Reactor Featuring an Endothermic Reaction", AIChE 20th National Heat Transfer Conference, Milwaukee, Wis., Aug. 2-5, 1981.

SUMMARY OF THE INVENTION

The apparatus and process of the present invention provides a plurality of vertically arranged fluidized bed zones with each fluidized bed zone having a baffle base plate with a plurality of apertures therethrough defining its lower boundary, the fluidized bed zone having within such zone a dense homogeneous fluidized bed with a voidage space above it. At least one downcomer conduit extends from the lower portion of one of the fluidized bed zones to the lower portion of a lower fluidized bed zone for solids transfer to the lower bed. The pressure gradients in the fluidized beds of this invention are linear even at high superficial gas velocities of three times the terminal velocity of the particles, and each fluidized bed forms a dense, homogeneous and stable phase. The apparatus and process of the present invention through the design of its downcomers, achieves a dense phase and a voidage space above each dense phase with solids of particle sizes having an average diameter of under 100 micrometers with attainment of homogeneous fluidization and control of solids mixing with high solids transfer between vertically arranged beds. The apparatus and process of this invention, while providing divided fluidized beds with countercurrent contact between solids and gases utilizing coarse particle (greater than 200 micrometers) fluidized beds, has its principal advantages in utilization of fine particle fluidized beds of less than 100 micrometers average particle diameter. The apparatus and process of this invention, utilizing fine particle fluidized beds, are particularly advantageous in utilization of multiple fluidized beds in chemically catalyzed systems to achieve high selectivity. The retention time of gas in a single bed according to the present invention is much less than prior conventional fluidized beds.

It is an object of this invention to provide an apparatus and process for conducting reactions in fluidized beds wherein, even at high superficial gas velocities of up to three times higher than the terminal velocity of the particles, the pressure gradient along the vertical axis of the bed is linear.

It is another object of this invention to provide an apparatus and process having a plurality of vertically arranged fluidized bed zones and having within each such zone a dense, homogeneous fluidized bed with a voidage space above it.

Another object of this invention is to provide a plurality of vertically arranged fluidized beds having high degree of solids circulation flow between the beds.

It is yet another object of this invention to provide an apparatus and process for conducting reactions in fluidized solids having a plurality of vertically arranged fluidized bed zones providing countercurrent contact between the solids and gas.

It is another object of this invention to provide an apparatus and process for conducting reactions in a plurality of vertically arranged fluidized bed zones wherein the degree of gas back mixing may be controlled.

It is still another object of this invention to provide an apparatus and process for conducting reactions in a plurality of vertically arranged fluidized bed zones which may be readily scaled up from laboratory or pilot plant scale to commercial scale without changing the characteristics of the system.

BRIEF DESCRIPTION OF THE DRAWING

These and other objects, advantages and features of this invention will be apparent from the description and by reference to the drawing wherein preferred embodiments are shown as:

FIG. 1 is a schematic sectional view of a multiple fluidized bed system with downcomers according to one embodiment of this invention;

FIG. 2 is a schematic perspective view of another embodiment of a multiple fluidized bed system with downcomers and risers according to another embodiment of this invention; and FIG. 3 is a schematic sectional view of a multiple vertical and mutiple horizontal fluidized bed system according to another embodiment of this invention.

DESCRIPTION OF THE PREFERRED EMBODIMENTS

FIG. 1 shows fluidized bed reactor 10 contained within vessel 11 with fluidizing gas inlet conduit 12 in its lower portion. A similar fluidizing gas outlet conduit is provided at the upper end of vessel 11 for removal of the fluidizing gas flowing upwardly through fluidized bed reactor vessel 11. Control and pressurizing of the fluidizing gas will not be described in detail as any suitable pressurizing and control valve means may be utilized to obtain the desired flow rate of fluidizing gas through the fluidized bed reactor. Likewise, recycle of fluidizing gas and removal of particulate solids therefrom is well known in the art and will not be further discussed in this disclosure since the extent of removal of particulates is dependent upon the particular reaction concerned. Baffle base plates 13, denoted as 13A, 13B and 13C for the different beds, are provided at vertically spaced intervals substantially across the cross section of vessel 11 forming a lower boundary for each fluidized bed zone. Each baffle base plate has a plurality of apertures 14, denoted as 14A, 14B and 14C for the different beds, allowing upward passage of the fluidizing gas therethrough. The configuration of apertures 14 may be any desired shape known to the art and both the size of the individual apertures and the total aperture area of each baffle base plate may be the same or may be different to obtain the desired relationships between the plurality of fluidized beds, depending upon the solid particle size, whether or not risers are present, the downcomer cross-sectional area, and the desired solid particle residence time in each fluidized bed.

FIG. 1 shows three fluidized bed zones each comprising a dense homogeneous fluidized solids bed volume denoted as 20A, 20B, and 20C, and each comprising a voidage volume above the fluidized solids bed denoted as 21A, 21B, and 21C. The fluidized beds are schematically illustrated in FIG. 1 in their fluidized state due to sufficient velocity of the fluidization gas to maintain the solids in fluidized condition. As shown in the embodiment of the invention of FIG. 1, riser conduits are not used for the upward transport of solids from a lower to an upper fluidized bed, but the movement of solids from the lower to the next adjacent upper fluidized bed is effected by the solid particle being entrained in the fluidizing gas stream in passing from the lower to the next upper fluidized bed as shown by the arrows. In the embodiment shown in FIG. 1 solid particles are transported downwardly in downcomers 15A, 15B and 15C extending from the lower portion of an immediately adjacent upper fluid bed into the lower portion of solid fluidized beds 20A, 20B and 20C, respectively. An important feature of this invention is the large quantity of movement of solid particles between the vertical beds achieved by the downcomers extending from the lower portion of an upper bed zone to the lower portion of a lower fluidized bed zone. I have found it to be an important feature of this invention that the downcomer top opening 16 and the downcomer bottom opening 17, both indicated with respect to downcomer 15A, be located in the lower 20 percent of the height of the fluidized bed zone to best achieve the advantages of this invention. As shown, top opening 16 is directly in the baffle base plate. In a preferred embodiment, the top opening of the downcomer is in the baffle base plate and the lower opening of the downcomer is in the lower 10 percent of the height of the fluidized bed zone. I have found that with the downcomer in the described position, the circulation flow amount of solid particles between fluidized bed zones is determined by the design of the downcomer conduit. In accordance with the present invention, increasing the downcomer diameter increases the circulation volume of solid particles. In another embodiment, the downcomer may be an annular passage along the containment vessel having a top opening in the lower portion of one of the fluidized bed zones and extending to the lower portion of a lower fluidized bed zone.

Operation of the process schematically shown in FIG. 1 may be carried out with any desired solid particulate material, the size being dependent upon the density of the material used, but the particle must be sufficiently small to attain the desired entrainment in the upward flowing fluidizing gas to transfer sufficient solid particles in an upward direction between the beds while still maintaining a discreet, dense, homogeneous fluidized solids bed volume. Generally, particles having average diameters of less than about 100 micrometers are suitable for use in this invention without risers. According to this invention, it is desired that the average retention time of particles in a single fluidized bed can be controlled to be about 10 to about 50 seconds, preferably about 25 to about 35 seconds. The particulate retention time is determined by the total downcomer area, the total baffle base plate aperture area, the fluidized bed cross-sectional area, and the fluidizing gas velocity with any specific solid particulate material. If desired for particular processes, the average solids retention time in each of the fluidized beds may be different by varying the downcomer area and the baffle plate aperture area for the different beds as well as varying the major particulate material in the different vertical beds. While one downcomer is illustrated in FIG. 1 for each fluidized bed, it is readily apparent that any number of downcomers may be used to achieve the volume, rate, and distribution of downward particulate flow required for various processes to be conducted in the fluidized beds. Generally, one to about six downcomers per fluidized bed are suitable. The high volumetric circulation of particles between the fluidized beds is an important feature in attaining homogeneous fluidization at higher superficial gas velocities. The fluidized beds in accordance with this invention function quite differently from conventional multi-stage fluidized beds, enabling maintenance of a stable dense fluidized condition at much higher gas velocities by increasing and controlling the circulation rate of solid particles between multiple fluidized bed units. Desired homogeneous fluidization conditions can thus be attained in each of the fluidized bed units.

FIG. 2 schematically shows another apparatus according to this invention which is similar to the apparatus shown in FIG. 1 except that it is provided with riser conduits 25 having riser bottom openings 27 in the upper portion, preferably in the upper ten percent of the height of the fluidized bed, or above the surface of the lower fluidized bed and riser top openings 26 in the lower portion of an upper fluidized bed. The riser conduits enhance the upward transfer of solids and are necessary when larger solids are used in the fluidized beds. While the geometry shown in FIG. 2 has the riser conduit in line with the downcomer conduit, this is not necessary and the riser and downcomer conduits may be located at different positions in the baffle base plate and multiple risers or multiple downcomers may be used in each stage, as necessary to obtain desired solids transport.

FIG. 3 shows another embodiment of this invention having horizontal sets of multiple vertically arranged fluidized beds 20A1, 20B1 and 20C1 with vertical partition 30 which have openings 31 separating them from similar multiple vertical fluidized beds 20A2, 20B2 and 20C2, respectively. The configuration shown in FIG. 3 allows for both vertical and horizontal transfer of solids between discreet homogeneous fluidized beds according to this invention. The horizontal transfer of solids essentially maintains equal height of horizontally adjoining beds. The downcomer and riser conduits as shown in FIG. 3 are the same as shown and described with respect to FIG. 2. Horizontal sets of multiple vertically arranged fluidized bed zones according to this invention provide assured scale-up ability to commercial plant sized units having very similar characteristics to a laboratory or pilot plant scale unit.

When smaller solid particles, about 100 micrometers and less, are used in fluidized bed systems according to this invention, upward transport of solids may be a combination of entrainment in the fluidizing gas and in riser conduits as shown by the arrows in FIG. 3. The upward transport of solids may be through a riser extending through upper adjacent bed(s) to an upper, non-adjacent bed. Likewise, the downward transport of solids may be through a downcomer extending through the lower adjacent bed(s) to a lower, non-adjacent bed.

The fluidized beds of this invention achieve homogeneous fluidization with dense fluidized beds. Due principally to the homogeneous dense fluidized beds attainable with this invention, scale-up ability from laboratory or pilot plant scale to full plant scale is readily attainable with the full plant scale fluidized bed functioning in the same fashion as the laboratory scale fluidized bed. The fluidized beds of this invention provide controlled mixing characteristics of solids and gases with intimate solids-gas contact. The plurality of vertically arranged fluidized beds according to this invention with high volume solids transfer between the beds renders gas-solid countercurrent contact attainable. The fluidized beds of this invention attain all of the above characteristics in a multiple bed system which have not been previously attained with prior art systems, particularly with small solids having average diameters of generally under 100 micrometers.

Suitable materials for construction of an apparatus of this invention will be recognized by persons skilled in the art and will not be discussed in this disclosure due to the large variation in suitable materials caused by the wide variety of either thermal or chemical reactions which may be carried in the apparatus of this invention.

The following specific examples are set forth as exemplary of specific embodiments of this invention and use of specific materials or conditions is not meant to limit the invention.

EXAMPLE I

To show a plurality of vertically arranged fluidized bed zones in accordance with one embodiment of this invention, a vessel having a diameter of 5 centimeters and height of 350 centimeters was constructed with base baffle plates and downcomers as shown in FIG. 1. The unit had 12 baffle base plates equally spaced at 6 centimeters apart. Each baffle base plate had 10 round riser openings, each having a diameter of 0.5 centimeters. The lowermost of the baffle base plates was provided with a gas distributor for fluidizing gas. One downcomer, as shown in FIG. 1, extending from an upper baffle base plate downwardly for 5 centimeters and having a diameter of 2.5 centimeters was installed on each of the baffle base plates except the lowermost. Solid particles of Fluid Catalytic Cracking Catalyst having particle diameters of 65 microns were loaded to a height of 30 centimeters from the lowermost baffle base plate. The minimum fluidization velocity was 0.25 centimeters per second at 20° C. and the superficial gas velocity was 30 centimeters per second at 20° C. Under the above operating conditions the pressure distribution along the vertical axis of the fluidized system was measured and expressed as the pressure difference of the location measured from atmospheric pressure in millimeters of water. Table I summarizes the results.

TABLE I

| Distance of Measurement Above Gas Distribution (cm) | ΔP (mmH₂O) |
|---|---|
| 29 | 218 |
| 59 | 178 |
| 89 | 138 |
| 119 | 98 |
| 149 | 58 |
| 179 | 18 |
| 209 | 0 |

The data in Table I shows that under the fluidizing conditions and the apparatus according to this invention well stabilized fluidized bed conditions can be attained. A stabilized fluidized bed was formed in each fluidized bed zone.

By contrast, a conventional fluidized bed using the same particles but without any baffle base plates or any downcomers was subjected to attempted fluidization under the same conditions of fluidization and due to intensive slugging phenomena no stabilized fluidized bed was formed.

EXAMPLE II

To show the control of gas of gas back mixing according to the apparatus and process of this invention, a vessel having a diameter of 15 centimeters and height of 240 centimeters was fitted with 6 baffle base plates at intervals of 30 centimeters between base plates. Each baffle base plate had 15 riser openings of 1.3 centimeters in diameter. One downcomer conduit extended from each upper baffle base plate for 29 centimeters downwardly, having its bottom opening one centimeter above the lower baffle base plate, and having a diameter of 7 centimeters. Fluid Catalytic Cracking Catalyst Particles having an average size of 65 microns in diameter were loaded to provide a bed height of 90 centimeters before fluidization. The minimum fluidization velocity was 0.25 centimeters per second at 20° C. and superficial gas velocity was 20 centimeters per second at 20° C. Tracer $CO_2$ gas was injected into the fourth fluidized bed zone above the gas distributor at the lowermost baffle base plate and concentrations of the $CO_2$ gas in the vertical direction at a steady state were measured. Based upon these measurements, the gas back mixing coefficients were calculated according to the method set forth in Zuiderweg, F. J. "mixing" in Davidson, J. F. et al, Fluidization, 347, New York, Academic Press, 1971. A second fluidized bed was formed without any baffle base plates or downcomers and tracer gas injected at the same height position and the back mixing coefficients calculated. The gas back mixing coefficient for the fluidized bed system according to this invention was calculated to be 60 centimeters squared per second while the gas back mixing coefficient in a corresponding single conventional fluidized bed was calculated to be 500 centermeters squared per second. Thus, it has been shown that the gas back mixing coefficient can be retained at a low level by use of the apparatus and process of this invention.

EXAMPLE III

A plurality of vertically arranged fluidized bed zones were arranged in a containment vessel having a diameter of 10 centimeters and a height of 300 centimeters. Six baffle base plates were installed with the interval distance between the baffle base plates of 30 centimeters. Each baffle base plate had 12 riser openings, each having a diameter of 1.2 centimeters. Each fluidized bed zone, except the lowermost fluidized bed zone, had 1 downcomer conduit extending from the baffle base plate immediately above that zone downwardly 27 centimeters and had a diameter of 5 centimeters.

The fluidized bed system was used for the catalytic dehydrogenation of propane to yield propylene. The catalyst used was $Cr_2O_3$ 7 weight percent and $Al_2O_3$ (gamma crystaline form) 93 weight percent. The average particle size was 70 microns. The unit was filled with solid catalyst particles to a bed height of 90 centimeters before fluidization. The minimum fluidization gas velocity was 0.3 centimeters at 620° C. and the superficial gas velocity was 30 centimeters per second at 620° C.

A second single conventional fluidized bed of the same particles and conducted under the same reaction conditions was used as a comparison in the catalytic dehydrogenation of propane to propylene at 620° C.

Table III shows the data obtained using the plurality of vertically arranged fluidized bed zones according to this invention compared with a single conventional fluidized bed.

TABLE III

| | Plurality of Vertically Arranged Fluidized Beds | Conventional Single Fluidized Bed |
|---|---|---|
| Conversion (%) | 52.9 | 53.1 |
| Selectivity (%) | 75.4 | 60.2 |
| Yield in one Pass (%) | 40.0 | 32.0 |

Table III shows the selectivity utilizing the apparatus and process of this invention was significantly increased. The increase in selectivity is probably the result of reduced gas back mixing which results in the unfavorable secondary reaction of cracking of propylene. It is also noted that the one pass yield is increased by as much as 25 percent.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. Apparatus for conducting reactions in fluidized solids comprising:
   a vessel defining a continuous upward flow path for fluidizing gas sequentially through a plurality of vertically arranged fluidized bed zones;
   means for introducing said fluidizing gas in a lower portion of said vessel and means for removing said fluidizing gas in an upper portion of said vessel;
   a plurality of vertically arranged fluidized bed zones, each said fluidized bed zone having a baffle base plate having a plurality of apertures therethrough defining the lower boundary thereof, a dense homogeneous fluidized bed of said solids supported by said base plate, and a voidage space above said dense homogeneous fluidized bed extending to the lower boundary of an upper said vertically arranged fluidized bed zone;

at least one downcomer conduit for downward passage of said solids having a top opening in the lower portion of one of said dense fluidized beds, said downcomer conduit extending to and having a bottom opening in the lower portion of a lower of said dense fluidized beds and at least one riser conduit for upward pasage of said solids having a bottom opening in the upper portion or above the surface of one of said fluidized beds, said riser conduit extending to and having a top opening in the lower portion of an upper of said fluidized beds, and said riser conduit having a larger diameter than said apertures in said base plates.

2. The apparatus of claim 1 wherein each said downcomer conduit top opening and said downcomer conduit bottom opening is located in the lower twenty percent of the height of the respective fluidized bed zone.

3. The apparatus of claim 1 wherein each said downcomer conduit top opening and said downcomer conduit bottom opening is located in the lower ten percent of the height of the respective fluidized bed zone.

4. The apparatus of claim 1 wherein each said downcomer conduit top opening is directly in a baffle base plate and said downcomer conduit bottom opening is located in the lower ten percent of the height of the lower fluidized bed zone.

5. The apparatus of claim 1 or 2 or 3 having more than one said downcomer conduit in each fluidized bed zone.

6. The apparatus of claim 1 or 2 or 3 wherein said downcomer conduit comprises an annular conduit at the periphery of said fludized bed zones.

7. The apparatus of claim 1 or 4 wherein said downcomer conduits extend through a vertically adjacent fluidized bed zone to a lower, non-adjacent fluidized bed zone.

8. The apparatus of claim 1 wherein said at least one riser conduit bottom opening is located in the upper twenty percent of the height of said fluidized bed.

9. The apparatus of claim 1 wherein said at least one riser conduit bottom opening is located above the surface of said fluidized bed.

10. The apparatus of claim 1 wherein said at least one riser conduit top opening is directly in the baffle base plate.

11. The apparatus of claim 1 comprising horizontal sets of said plurality of vertically arranged fluidized bed zones, said horizontal sets of fluidized bed zones separated by vertical partitions.

12. The apparatus of claim 11 wherein said vertical partitions have openings providing communication between horizontally adjacent fluidized beds.

13. The apparatus of claim 1 wherein said at least one riser conduit top opening is located in the lower ten percent of the height of the respective bed.

14. The apparatus of claim 1 or 3 or 4 or 13 wherein said downcomer conduits extend to vertically adjacent fluidized bed zones.

15. The apparatus of claim 9 or 13 wherein said downcomer conduits and said riser conduits extend through a vertically adjacent fluidized bed zone to a lower and upper, respectively, non-adjacent fluidized bed zone.

16. A process for conducting reactions in fluidized solids comprising:

maintaining a continuous upward flow of fluidizing gas sequentially through a plurality of vertically arranged fluidized bed zones, each said fluidized bed zone having a baffle base plate having a plurality of openings defining the lower boundary thereof, at a velocity to maintain solids in a dense homogeneous fluidized bed in fluidized condition and to maintain a free voidage volume above said fluidized bed in each said fluidized bed zone;

mixing solids downwardly between said fluidized bed zones by passing solids in downcomer conduits from the lower portion of one of said fluidized bed zones to the lower portion of a lower of said fluidized bed zones; and mixing solids upwardly between fluidized bed zones by passage of solids through at least one riser conduit having a bottom opening in the upper portion or above the surface of one of said fluidized beds, said riser conduit extending to and having a top opening in the lower portion of an upper of said fluidized beds, and said riser conduit having a larger diameter than said openings in said base plates.

17. The process of claim 16 wherein said downcomer conduit top and bottom opening is in the lower twenty percent of the height of the respective fluidized bed zone.

18. The process of claim 16 wherein said downcomer conduit top and bottom opening is in the lower ten percent of the height of the respective fluidized bed zone.

19. The process of claim 16 wherein each said downcomer conduit top opening is directly in a baffle base plate and said downcomer conduit bottom opening is located in the lower ten percent of the height of the lower fluidized bed zone.

20. The process of claim 16 having more than one said downcomer conduit in each fluidized bed zone.

21. The process of claim 16 wherein said downcomer conduit comprises an annular conduit at the periphery of said fluidized bed zones.

22. The process of claim 16 wherein said at least one riser conduit top opening is directly in the baffle base plate.

23. The process of claim 16 having horizontal sets of said plurality of vertically arranged fluidized bed zones and passing said fluidized solids between horizontally adjacent fluidized beds to maintain substantially equal fluidized bed heights in said horizontally adjacent fluidized beds.

24. The process of claim 16 wherein said downcomer conduits extend to vertically adjacent fluidized bed zones.

25. The process of claim 16 wherein said downcomer conduits extend through a vertically adjacent fluidized bed zone to a lower, non-adjacent fluidized bed zone.

26. The process of claim 16 wherein said fluidized solids comprise particles having average diameters less than 100 micrometers.

27. The process of claim 16 wherein the average retention time of solids in a single fluidized bed zone is about 10 to about 50 seconds.

28. The process of claim 16 wherein the average retention time of solids in a single fluidized bed zone is about 25 to about 35 seconds.

* * * * *